US010431879B2

(12) United States Patent
Kitchener et al.

(10) Patent No.: US 10,431,879 B2
(45) Date of Patent: Oct. 1, 2019

(54) FABRIC ANTENNA

(71) Applicant: BAE SYSTEMS plc, London (GB)

(72) Inventors: Dean Kitchener, Chelmsford (GB); Christopher Bryce Wyllie, Chelmsford (GB); Robert Alan Lewis, Chelmsford (GB); Ingrida Juraite, Chelmsford (GB); Tilak Dias, Nottingham (GB); William Hurley, Nottingham (GB)

(73) Assignee: BAE SYSTEMS plc, London (GB)

( * ) Notice: Subject to any disclaimer, the term of this patent is extended or adjusted under 35 U.S.C. 154(b) by 102 days.

(21) Appl. No.: 15/558,930

(22) PCT Filed: Mar. 11, 2016

(86) PCT No.: PCT/GB2016/050671
§ 371 (c)(1),
(2) Date: Sep. 15, 2017

(87) PCT Pub. No.: WO2016/146977
PCT Pub. Date: Sep. 22, 2016

(65) Prior Publication Data
US 2018/0076510 A1 Mar. 15, 2018

(30) Foreign Application Priority Data

Mar. 18, 2015 (GB) .................................. 1504629.5
Apr. 21, 2015 (EP) .................................... 15275123

(51) Int. Cl.
*H01Q 1/52* (2006.01)
*H01Q 1/27* (2006.01)
(Continued)

(52) U.S. Cl.
CPC ............. *H01Q 1/273* (2013.01); *A41D 27/00* (2013.01); *D02G 3/44* (2013.01); *H01Q 1/22* (2013.01);
(Continued)

(58) Field of Classification Search
CPC .......... H01Q 1/526; H01Q 1/273; H01Q 7/00; H01Q 9/26; H01Q 1/1207; H01Q 1/44
(Continued)

(56) References Cited

U.S. PATENT DOCUMENTS 5,906,004 A 5/1999 Lebby et al.
6,727,197 B1 4/2004 Wilson et al.
(Continued)

FOREIGN PATENT DOCUMENTS

WO 2014138204 A1 9/2014
WO 2016146977 A1 9/2016

OTHER PUBLICATIONS

International Search Report and Written Opinion received for Patent Application No. PCT/GB2016/050671, dated Jun. 14, 2016. 16 pages.
(Continued)

*Primary Examiner* — Hai V Tran
*Assistant Examiner* — Collin Dawkins
(74) *Attorney, Agent, or Firm* — Finch & Maloney PLLC

(57) ABSTRACT

A fabric antenna for telecommunications is disclosed. The fabric antenna comprises a host yarn, which is substantially electrically non-conducting, and an antenna yarn, which is substantially electrically conducting. The host yarn and antenna yarn are knitted together to form a host fabric comprising an antenna grid. The antenna grid comprises a plurality of intersecting antenna tracks formed of antenna yarn. The tracks are separated by regions of the host fabric and are electrically coupled together at the regions where the tracks intersect.

20 Claims, 4 Drawing Sheets

(51) Int. Cl.

| | |
|---|---|
| ***H01Q 1/22*** | (2006.01) |
| ***A41D 27/00*** | (2006.01) |
| ***D02G 3/44*** | (2006.01) |
| *H01Q 9/40* | (2006.01) |
| *H01Q 5/371* | (2015.01) |

(52) U.S. Cl.
CPC ............... *H01Q 1/27* (2013.01); *H01Q 5/371* (2015.01); *H01Q 9/40* (2013.01)

(58) Field of Classification Search
USPC .................. 343/841, 718, 878, 908; 112/439
See application file for complete search history.

(56) References Cited

U.S. PATENT DOCUMENTS 7,461,444 B2 * 12/2008 Deaett ..................... H01P 11/00 29/600
2004/0115430 A1 6/2004 Leonard
2005/0235482 A1 10/2005 Deaett et al.
2006/0281382 A1 12/2006 Karayianni et al.
2009/0159149 A1 * 6/2009 Karayianni .......... D03D 1/0088 139/425 R
2011/0214711 A1 9/2011 Hauser et al.
2014/0103116 A1 4/2014 Martin et al.
2014/0170920 A1 6/2014 Manipatruni et al.
2014/0318699 A1 * 10/2014 Longinotti-Buitoni ...................... A61B 5/0002 156/247
2014/0363656 A1 * 12/2014 Kunisada ............... D02G 3/441 428/221

OTHER PUBLICATIONS

International Preliminary Report on Patentability received for Patent Application No. PCT/GB2016/050671, dated Jun. 12, 2017. 11 pages.

GB Intellectual Property Office Search Report under Section 17(5) received for GB Patent Application No. 1504629.5 dated Jul. 9, 2015. 3 pages.

Extended European Search Report, pursuant to Rule 62 EPC, received for EP Patent Application No. 15275123.6 dated Oct. 23, 2015. 10 pages.

Paul, et al., "Textile Broadband E-Patch Antenna at ISM Band," Antennas and Propagation for Body-Centric Wireless Communications, 2007. pp. 38-43.

Roh, et al., "Embroidered Wearable Multiresonant Folded Dipole Antenna for FM Reception," IEEE Antennas and Wireless Propagation Letters, vol. 9., 2010. pp. 803-806.

* cited by examiner (a)

(b)

FABRIC ANTENNA

The present invention relates to a fabric antenna.

It is known to provide a garment with an antenna, such that the antenna can be worn by a user. Such antennas include an electrically conductive sheet, such as a Nora Dell sheet material, which may be ironed onto the surface of a t-shirt, for example. However, it is often difficult to electrically couple the sheet with a communications cable for enabling communications using the antenna. In addition, the sheet material has a relatively high optical reflectivity, which reduces the covertness of the garment. It is also found that the sheet material lacks sufficient strength to be suitably sewn onto a garment and degrades during washing of the garment or normal wear and tear expected of such a garment.

According to a first aspect of the present invention there is provided a fabric antenna for communications, the fabric antenna comprising a host yarn, which is substantially electrically non-conducting, and an antenna yarn, which is substantially electrically conducting, the host yarn and antenna yarn being knitted together to form a host fabric formed of host yarn comprising an antenna grid formed of antenna yarn, the antenna grid comprising a plurality of intersecting antenna tracks, the tracks being separated by regions of the host yarn, the tracks of the antenna grid being electrically coupled together at the regions where the tracks intersect.

Advantageously, the grid nature of the antenna provides for an increased flexibility in the fabric, whereas the knitted form of the antenna yarn with the host yarn provides for a secure coupling of the antenna with the host fabric which can be subsequently sewn onto a garment, for example.

In an embodiment, the antenna grid comprises a plurality of grid sections, each section comprising a first and second side track and a first and second end track which separately extend between opposite ends of the first and second side tracks to form a closed periphery of the grid section. Each section further comprises a central track which extends along a central axis of the respective grid section and a plurality of intermediate cross tracks which extend across the central track, between side tracks.

Preferably, the end tracks and cross tracks are electrically coupled to each side track and the central track, and the grid sections are electrically coupled to each other. It is envisaged that the electrical coupling may be formed by the intimate contact of the knitted antenna yarn at the intersecting points.

In an embodiment, each grid section comprises a rectangular periphery and the grid sections are configured within the host fabric to form an F-shaped antenna grid.

In an embodiment, the antenna tracks of the antenna grid comprise a square arrangement of intersecting tracks.

In an embodiment, the antenna tracks may comprise a course or wale of knitted stitches in the host fabric. The number of knitted stitches of host yarn per unit length of the fabric is preferably greater than the number of knitted stitches of antenna yarn per unit length of fabric. The reduced number of stitches of antenna yarn provides for a more flexible fabric and reduces the length of antenna yarn required to create the antenna.

In an embodiment, one or more of the antenna tracks may be formed by two or more adjacent courses or wales of knitted stitches.

The fabric antenna further comprises an antenna ground, which comprises a ground grid formed of ground yarn which is substantially electrically conducting, the ground yarn and host yarn being knitted together to form a host fabric comprising the antenna ground.

The ground yarn and host yarn may be knitted together to form a single layer of host fabric. Thereby, providing a thinner antenna ground that is less bulky and which is more comfortable for a user to wear.

In an embodiment, the ground grid is knitted adjacent the antenna grid and comprises a plurality of intersecting ground tracks, similar to the antenna grid.

The ground grid comprises a closed periphery of ground tracks and a plurality of longitudinal and lateral ground tracks which extend within the periphery to form a square arrangement of intersecting ground tracks. The peripherally extending ground tracks, longitudinal ground tracks and lateral ground tracks are preferably electrically coupled together at the regions of intersection.

In an embodiment, the ground tracks may comprise a course or wale of knitted stitches in the host fabric. The number of knitted stitches of host yarn per unit length of the fabric is preferably greater than the number of knitted stitches of ground yarn per unit length of fabric. The reduced number of stitches of ground yarn similarly provides for a more flexible fabric and reduces the length of ground yarn required to create the antenna ground.

Preferably, the antenna grid and ground grid extend in substantially the same plane.

In an embodiment, one or more of the ground tracks may be formed by two or more adjacent courses or wales of knitted stitches.

In an embodiment, the antenna yarn and/or ground yarn comprises AmberStrand®.

The fabric antenna may comprise a lining to a garment, such as a jumper or t-shirt or be incorporated with a power and data distribution harness arranged to be worn on a user's body or incorporated within a tactical vest for wearing by a user, such that the garment may form a body worn antenna.

At least one track of the antenna grid preferably extends beyond the periphery of the antenna grid and terminates at a connector for connecting the antenna grid to a communications cable, for example a coaxial cable. The communications cable may extend to a communications module held within a bag which may be carried by a wearer of the fabric antenna, for example. Alternatively, the communication cable may extend to a power and/or data distribution harness to be worn by a user such that the antenna is connected to a communications module via the communication cable and distribution harness. The harness may be incorporated within a tactical vest to be worn by a user.

The antenna yarn and host yarn may be knitted together to form a single layer of host fabric. Thereby providing a thinner fabric antenna that is less bulky and which is more comfortable for a user to wear.

The intersecting antenna tracks may be arranged to form a single antenna element. Such that the fabric may comprise a single antenna element with a ground plane that is in substantially the same plane as the single antenna element.

According to a second aspect of the present invention there is provided a garment comprising an outer layer of fabric material and a lining comprising a fabric antenna of the first aspect.

In an embodiment, the garment further comprises a pocket for supporting a communications cable which is used for connecting the fabric antenna to a communications module.

In an embodiment, the pocket is disposed on an interior side of the garment, such as upon the lining.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments.

Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

The invention may be performed in various ways, and, by way of example only, embodiments thereof will now be described, reference being made to the accompanying drawings in which.

Figure 4:
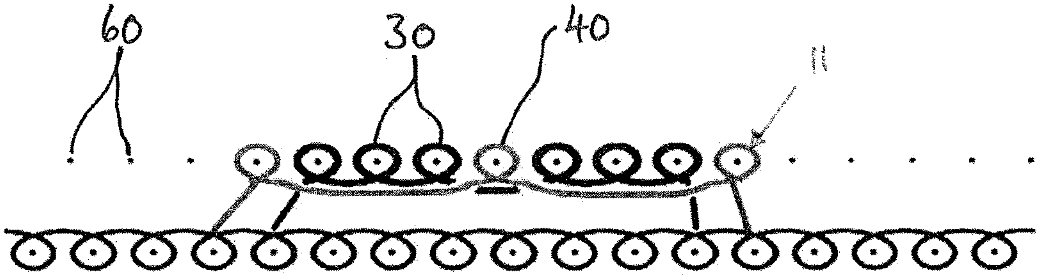
Figure 4:
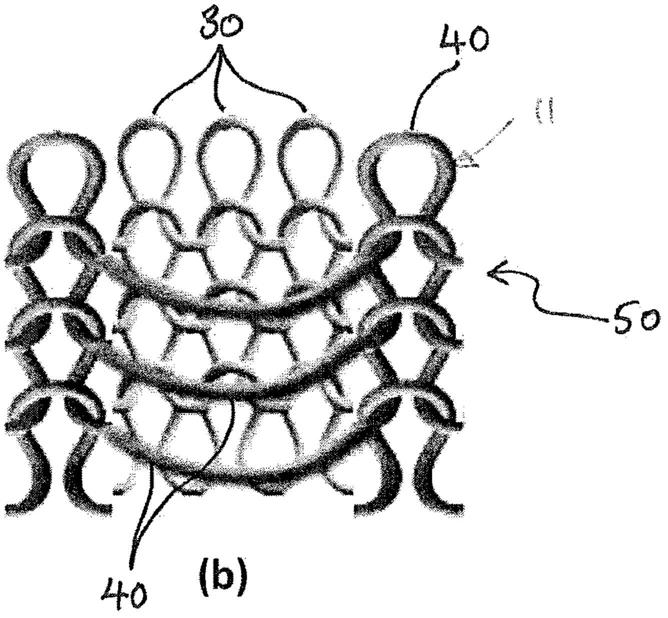

FIG. 4*a* is a schematic illustration of the stitches associated with the host yarn and the antenna or ground yarn of the fabric antenna; and, FIG. 4*b* is a magnified view of a portion of the fabric antenna, illustrating the stitches of the host yarn and antenna yarn.

Figure 1:
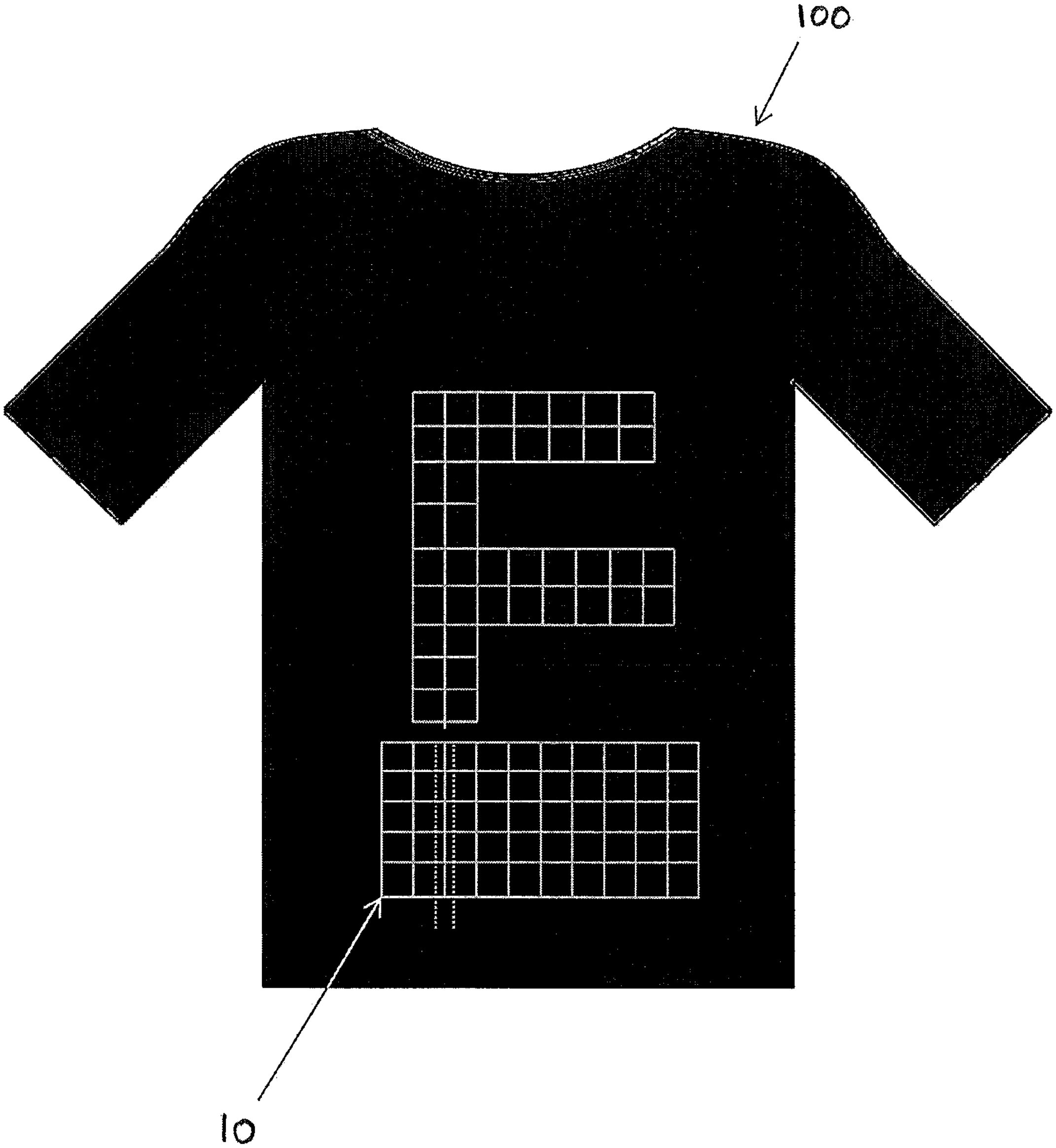
FIG. 1 is a front view of a t-shirt showing the location of a fabric antenna according to an embodiment of the present invention.
Figure 2:
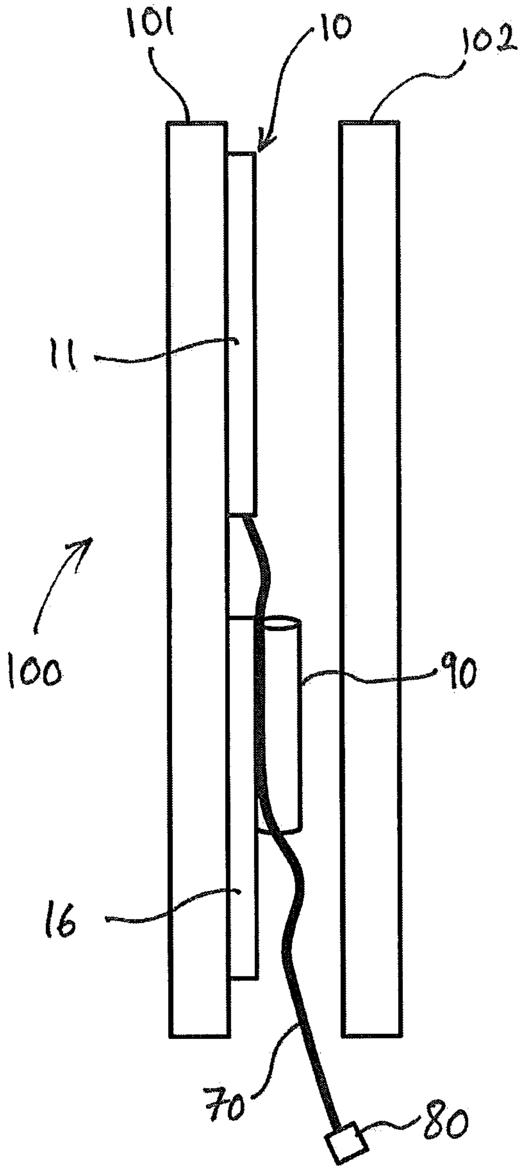
FIG. 2 is schematic side view of the t-shirt illustrated in FIG. 1, as worn by a user.

Referring to FIGS. 1 and 2 of the drawings, there is illustrated a fabric antenna 10 according to an embodiment of the present invention secured upon a garment 100, according to an embodiment of the present invention, for enabling communication with a third party (not shown) over a VHF (very high frequency) or UHF (ultra high frequency) range. The fabric antenna 10 illustrated in FIGS. 1 and 2 is disposed at an interior side of the garment so that the fabric antenna 10 is not readily visible and thus substantially concealed and/or protected by the outer fabric 101 of the garment (the fabric antenna 10 has been shown in FIG. 1 to illustrate the location of the antenna upon the garment). In this respect, the fabric antenna 10 may be sewn or bonded along an interior of the garment 100 and thus form a lining thereof, or may be sandwiched between an inner and outer layer 101, 102 of the garment 100.

Referring to FIGS. 4*a* and 4*b*, the fabric antenna 10 is formed by knitting together a host yarn 30, such as cotton which is substantially electrically non-conductive and an antenna yarn 40, such as AmberStrand® (as provided by Syscom Advanced Materials Inc. of Columbus, Ohio) or Statex (as provided by Statex Engineering (P) Ltd of Tamilnadu, India), which is substantially electrically conductive, to form a fabric 50 comprising the antenna 11. The knitted structure is formed by feeding the host yarn 30 and antenna yarn 40 into needles 60, shown in cross section in FIG. 4*a*, to create a series of knitted loops (as illustrated in FIG. 4*b* of the drawings). The loops which extend horizontally across the fabric form the so-called courses within the fabric 50, whereas the loops which extend vertically between adjacent courses form the wales within the fabric 50.

Like weaving, knitting is a technique for producing a two-dimensional fabric made from a yarn or thread. In weaving, threads are always straight, running parallel either lengthwise (warp) or crosswise (weft). By contrast, the yarn in knitted fabrics follows a meandering path (course), forming substantially symmetric loops (bights) which are substantially symmetrically above and below the mean path of the yarn. These meandering loops (wales) can be easily stretched in different directions giving knit fabrics much more elasticity than woven fabrics.

Figure 3:
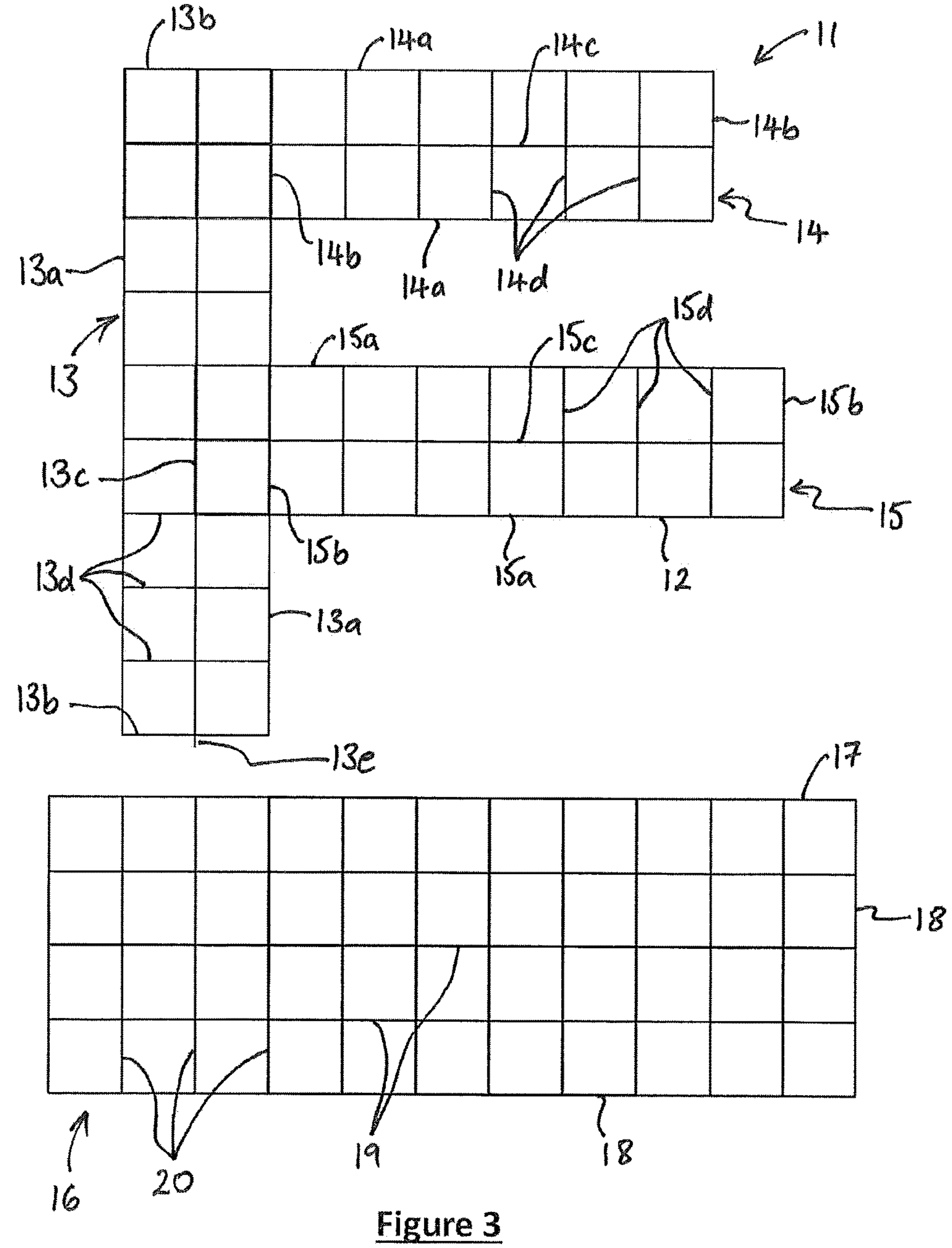
FIG. 3 is a view of the antenna grid and ground grid of the fabric antenna.

Referring to FIG. 3, the antenna 11 formed within the fabric 50 comprises an antenna grid 12 having a plurality of antenna tracks formed of antenna yarn 40 which extend along courses and wales within the fabric 50. The antenna grid 12 comprises three rectangular grid sections 13, 14, 15 which are orientated to form an F-shaped antenna 11.

The grid sections 13, 14, 15 separately comprise opposite side and end tracks 13*a*, 13*b*, 14*a*, 14*b*, 15*a*, 15*b* which are electrically coupled to form a substantially rectangular shaped periphery. In an embodiment, the outer periphery of the grid section 13 which forms the vertical portion of the F-shape comprises the largest (length×width) dimension of approximately 250×60 mm. In contrast, the outer periphery of the upper horizontal grid section 14 of the F-shape comprises a dimension of approximately 160×60 mm, whereas the outer periphery of the lower horizontal grid section 15 comprises a dimension of approximately 180×60 mm.

Each grid section 13, 14, 15 further comprises a central track 13*c*, 14*c*, 15*c* which extends along a central axis, such as the longitudinal axis of the grid section 13, 14, 15, and a plurality of cross tracks 13*d*, 14*d*, 15*d* which extend across the grid section 13, 14, 15 between opposite side tracks 13*a*, 14*a*, 15*a*. The end tracks 13*b*, 14*b*, 15*b* and cross tracks 13*d*, 14*d*, 15*d* are electrically coupled to each side track 13*a*, 14*a*, 15*a* and central track 13*c*, 14*c*, 15*c* by virtue of the intimate contact of the antenna yarn 30 at the intersections thereof. Moreover, the tracks 13*a-d*, 14*a-d*, 15*a-d* associated with each grid section 13, 14, 15 are electrically coupled together, such that an electrical signal which is to be communicated from the antenna 11 or received at the antenna 11, can access all of the tracks 13*a-d*, 14*a-d*, 15*a-d* of the antenna grid 12. However, the skilled reader will recognise that other antenna grids 12 forming other shapes may alternatively be used.

The electrical resistance of the antenna grid 12 is found to be different along the courses as opposed to along the wales of the fabric 50. This is because the resistance along a single course of antenna yarn 40 within the fabric 50 is determined by the resistance of the antenna yarn alone, whereas the resistance along a wale will also be influenced by the electrical coupling between adjacent courses of the antenna yarn 40. To improve the performance of the antenna 11, it is found that a lower resistance is required in the vertical direction, and so the F-shaped antenna grid is formed in a rotated configuration, namely a ¼ anticlockwise turn, so that the courses in the fabric 50 extend between the top and bottom of the F-shape.

The fabric antenna 10 further comprises an antenna ground 16 which is formed by knitting ground yarn (not shown), which may be the same as the antenna yarn 40, with the host yarn 30. The antenna ground 16 formed within the fabric 50 comprises a ground grid 17 having a periphery of ground tracks 18 and a plurality of longitudinal and lateral ground tracks 19, 20 which extend within the periphery 18 to form a square arrangement of intersecting ground tracks 18, 19, 20. The ground tracks 18, 19, 20 are formed of ground yarn (not shown) which extend along courses and wales within the fabric 50 and the peripherally extending ground tracks 18, longitudinal ground tracks 19 and lateral ground tracks 20 are preferably electrically coupled together at the regions of intersection.

The antenna ground 16 is knitted into the host fabric such that the ground 16 is disposed below the antenna 11 when in use, and thus in substantially the same plane. The central track 13*c* of the vertically orientated grid section 13 of the antenna grid 12 is arranged to extend beyond the periphery of the respective grid section 13 at the lower region thereof to form a tail 13*e*.

The tail 13*e* from the antenna grid 12 is coupled to a communications cable 70, such as a coaxial cable. In this respect, the tail 13*e* may be electrically coupled, such as via soldering to a proximal end of an inner conductor (not shown) of the coaxial cable. At least a portion of the outer conductor (not shown) of the coaxial cable is electrically coupled, such as via soldering and/or gluing directly to the one of the tracks of the ground grid. The distal end of the cable terminates at a connector 80, such as an SMA (subminiature A) connector for electrically connecting the antenna 11 to a communications module (not shown), which may be disposed in a bag (not shown) carried by a user, for example, or in the alternative, incorporated with a power and/or data distribution harness or attached to a tactical vest, for example. The fabric antenna 10 may further comprise a pocket 90 for supporting the cable 70 and minimising any snagging of the cable 70 during use.

In the illustrated embodiment, the intersecting tracks 13*a-d*, 14*a-d*, 15*a-d* of the antenna 11 and ground 16 are configured to a square grid, but the skilled reader will again recognise that other grid configurations may be used. Referring to FIGS. 4*a* and 4*b* of the drawings, the tracks of each grid 12, 17 may be separately formed by one or more adjacent courses or wales of antenna/ground yarn, such that the width of each track may be sized accordingly. The antenna yarn 40 and ground yarn (not shown) are knitted with the host yarn 30 according to a ⅓ knitting gauge whereby the antenna yarn 40 and ground yarn (not shown) are respectively looped around every fourth needle 60, in contrast with the host yarn 30 which is looped around every needle 60. In this respect, the antenna yarn 40 and ground yarn (not shown) are drooped between every fourth needle 60 and provide for a more flexible and thus wearable fabric 50. Moreover, the reduced number of needle loops associated with the antenna yarn 40 and ground yarn (not shown) reduces the length of antenna yarn 40 and ground yarn (not shown) required and reduces distortion in the fabric 50 caused by the antenna yarn 40 and ground yarn (not shown).

It will be understood, that the grid structure of the antenna grid 12 and the ground grid 17 is to be contrast with to conventional antenna designs that require continuous metal surfaces for both antenna and ground elements. Thereby, the fabric antenna 10 benefits from a reduction in cost and weight when compared with a conventional continuous metal surface element. Furthermore, the antenna and ground grids 12 and 17 allow flexibility to the fabric 50, thereby making the fabric 50 more comfortable to wear as the fabric 50 can stretch with a wearer's movements.

It will also be understood that the antenna grid 12 and ground grid 17 form a single layer with the fabric 50; thereby the fabric 50 is thinner than conventional antenna structures.

The antenna grid 12 and ground grid 17 are arranged such that they are in the same plane with respect to one another, rather than in conventional solid metal surface antenna element structures that have a ground plane arranged in a parallel plane to the plane of the antenna element. Again, the arrangement of the present invention provides the fabric 50 with a thinner structure than a conventional antenna structure.

Furthermore, using a grid structure for the antenna grid 12 and ground grid 17 also means that conductive yarn does not need to be knitted into a complete filled structure to form the antenna and ground, respectively. This mitigates "rucking" of yarn material that tends to occur across a completely filled structure. It will be understood that "rucking" refers to the bunching of yarns such that the material does not appear to flat across the surface of the material.

The invention claimed is:

1. A fabric antenna for telecommunications, the fabric antenna comprising:

a host yarn, which is substantially electrically non-conductive, and an antenna yarn, which is substantially electrically conductive, the host yarn and antenna yarn being knitted together to form a host fabric formed of host yarn comprising an antenna grid formed of antenna yarn, wherein the antenna grid comprises a plurality of intersecting antenna tracks formed of antenna yarn, the tracks being separated by regions of the host yarn, the tracks of the antenna grid being electrically coupled together at the regions where the tracks intersect, wherein the antenna grid comprises a plurality of grid sections, wherein a first grid section of the plurality of grid sections comprises a first side track, a second side track, a first end track, and a second end track, wherein the first end track and the second end track separately extend between opposite ends of the first side track and the second side tracks, and wherein the first side track, the second side track, the first end track, and the second end track form a closed periphery of the first grid section.

2. The fabric antenna according to claim 1, wherein the first grid section comprises:

one or more cross tracks, each of the one or more cross tracks extending between the first side track and the second side track.

3. The fabric antenna according to claim 2, wherein the grid sections are electrically coupled to each other.

4. The fabric antenna according to claim 2, wherein the first grid section comprises:

a central track extending between the first end track and the second end track, the central track intersection with the one or more cross tracks.

5. The fabric antenna according to claim 1, wherein the antenna grid comprises an F-shape.

6. The fabric antenna according to claim 1, wherein the antenna tracks comprise a course or wale of knitted stitches in the host fabric.

7. The fabric antenna according to claim 6, wherein the number of knitted stitches of host yarn per unit length of the host fabric is greater than the number of knitted stitches of antenna yarn per unit length of the host fabric.

8. The fabric antenna according to claim 6, wherein one or more of the antenna tracks are formed by two or more adjacent courses or wales of knitted stitches.

9. The fabric antenna according to claim 1 further comprising an antenna ground, which comprises a ground grid formed of ground yarn which is substantially electrically conductive, the ground yarn and host yarn being knitted together to form the host fabric comprising the antenna grid.

10. The fabric antenna according to claim 9, wherein the ground yarn and host yarn are knitted together to form a single layer of fabric.

11. The fabric antenna according to claim 9, wherein the ground grid is knitted adjacent the antenna grid and comprises a plurality of intersecting ground tracks.

12. The fabric antenna according to claim 11, wherein the ground tracks comprise a course or wale of knitted stitches in the host fabric.

13. The fabric antenna according to claim 12, wherein the number of knitted stitches of host yarn per unit length of the host fabric is greater than the number of knitted stitches of ground yarn per unit length of the host fabric.

14. The fabric antenna according to claim 9, wherein the ground grid comprises a closed periphery of ground tracks and a plurality of longitudinal and lateral ground tracks which extend within the periphery to form a rectangular or square arrangement of intersecting ground tracks.

15. The fabric antenna according to claim 1, wherein the intersecting antenna tracks are arranged to form a single antenna element.

16. The garment comprising an outer layer of fabric material and a lining comprising a fabric antenna according to claim 1.

17. The garment according to claim 16, further comprising a pocket for supporting a communications cable which is used for connecting the fabric antenna to a communications module.

18. The fabric antenna according to claim 1, wherein the first side track, the second side track, the first end track, and the second end track are arranged in a rectangular or square arrangement to form the closed periphery of the first grid section.

19. A fabric antenna for telecommunications, the fabric antenna comprising:

a host yarn, which is substantially electrically non-conductive; and an antenna yarn, which is substantially electrically conductive, wherein the host yarn and antenna yarn being knitted together to form a host fabric formed of host yarn comprising an antenna grid formed of antenna yarn, wherein the antenna grid comprising a plurality of intersecting antenna tracks formed of antenna yarn, the tracks being separated by regions of the host yarn, the tracks of the antenna grid being electrically coupled together at the regions where the tracks intersect, wherein the antenna yarn and host yarn are knitted together to form a single layer of host fabric, wherein the antenna grid comprises a plurality of grid sections, wherein each grid section comprises a first and second side track and a first and second end track which separately extend between opposite ends of the first and second side tracks to form a closed periphery of the grid section.

20. The fabric antenna according to claim 19 further comprising an antenna ground, which comprises a ground grid formed of ground yarn which is substantially electrically conductive, the ground yarn and host yarn being knitted together to form the host fabric comprising the antenna grid.

* * * * *